US008932521B2

(12) United States Patent
Kirsch et al.

(10) Patent No.: US 8,932,521 B2
(45) Date of Patent: *Jan. 13, 2015

(54) CHITOSAN-BASED HEMOSTATIC TEXTILE

(71) Applicant: Loma Linda University Medical Center, Loma Linda, CA (US)

(72) Inventors: Wolff M. Kirsch, Redlands, CA (US); Samuel Hudson, Raleigh, NC (US)

(73) Assignees: Loma Linda University Medical Center, Loma Linda, CA (US); North Carolina State University, Raleigh, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 14/097,151

(22) Filed: Dec. 4, 2013

(65) Prior Publication Data

US 2014/0093421 A1 Apr. 3, 2014

Related U.S. Application Data

(63) Continuation of application No. 12/954,572, filed on Nov. 24, 2010, now Pat. No. 8,623,274.

(60) Provisional application No. 61/264,570, filed on Nov. 25, 2009, provisional application No. 61/350,224, filed on Jun. 1, 2010.

(51) Int. Cl.
| | |
|---|---|
| A61L 2/00 | (2006.01) |
| A61L 26/00 | (2006.01) |
| A61L 33/08 | (2006.01) |
| A61L 15/28 | (2006.01) |
| A61L 24/00 | (2006.01) |
| A61L 24/08 | (2006.01) |
| A61L 31/04 | (2006.01) |

(Continued)

(52) U.S. Cl.
CPC ............. *A61L 26/0023* (2013.01); *A61L 33/08* (2013.01); *A61L 15/28* (2013.01); *A61L 24/0036* (2013.01); *A61L 24/08* (2013.01); *A61L 31/042* (2013.01); *A61L 2400/04* (2013.01); *A61L 2/20* (2013.01); *A61L 2/081* (2013.01)
USPC .............................................. 422/23; 422/28

(58) Field of Classification Search
None
See application file for complete search history.

(56) References Cited

U.S. PATENT DOCUMENTS

| | | |
|---|---|---|
| 4,321,232 A | 3/1982 | Bithell |
| 2004/0054346 A1 | 3/2004 | Zhu et al. |
| 2005/0038369 A1 | 2/2005 | Gregory et al. |

(Continued)

FOREIGN PATENT DOCUMENTS

CN          1833732 A          9/2006

OTHER PUBLICATIONS

M. Shobita Rao, Ramesh Chander, Aruin Sharma, "Radiation Processed Chitosan a Potent Antioxidant", Oct. 2006, 6 pages.

(Continued)

*Primary Examiner* — Brian Gulledge
(74) *Attorney, Agent, or Firm* — Knobbe Martens Olson & Bear LLP

(57) ABSTRACT

A microfibrillar high molecular weight chitosan-based textile can be used as a hemostat. The chitosan has been treated in a nitrogen field by applying energy to ionize nitrogen in and around the chitosan textile. A single or multiple such treatments may be employed. For example, the chitosan textile may be irradiated under nitrogen using γ-irradiation, treated under a nitrogen plasma, or both.

17 Claims, 5 Drawing Sheets

(51) Int. Cl.
A61L 2/20 (2006.01)
A61L 2/08 (2006.01)

(56) References Cited

U.S. PATENT DOCUMENTS

| | | |
|---|---|---|
| 2005/0058721 A1 | 3/2005 | Hursey |
| 2005/0107826 A1 | 5/2005 | Zhu et al. |
| 2005/0118238 A1 | 6/2005 | Zhu et al. |
| 2005/0123588 A1 | 6/2005 | Zhu et al. |
| 2006/0141060 A1 | 6/2006 | Hursey |
| 2007/0123816 A1 | 5/2007 | Zhu et al. |
| 2008/0064998 A1 | 3/2008 | Gregory et al. |
| 2008/0085300 A1 | 4/2008 | Huey et al. |
| 2008/0146984 A1 | 6/2008 | Campbell et al. |
| 2008/0241229 A1 | 10/2008 | Li et al. |
| 2008/0248508 A1 | 10/2008 | Baker et al. |
| 2009/0117213 A1 | 5/2009 | Beaulieu et al. |
| 2009/0137526 A1 | 5/2009 | Jubert |
| 2011/0306068 A1 | 12/2011 | Miller et al. |

OTHER PUBLICATIONS

U. Gryczka, D. Dondi, A.G. Chmielewski, W. Migdal, A. Buttafava, A. Faucitano, 170 "The mechanism of chitosan degradation by gamma and e-beam irradiation", 2008, 1 page.

Gyorgy Csake, Chao-Ming Tsal, Bronislaw L. Slominay, Anthony Herp, Ronald J. Elin, "Modification of the Chemical Composition and Structure of the U.S. Reference Standard Endotoxin (RSE) by Co Radiation", 1986, 13 pages.

Perola O. Magalhaes, Andre M. Lopes, Priscilla G. Mazzola, Carlota Rangel-Yagui, Thereza C. V. Penna, Adalberto Pessoa Jr., "Methods of Endotoxin Removal from Biological Preparations: a Review", 2007, 16 pages.

Brian D. Reid, "Gamma Processing Technology: An Alternative Technology for Terminal Sterilization of Parenterals", 7 pages.

S. Guyomard, V. Coury, J.C. Darbord, "Effects of Ionizing Radiations on Bacterial Endotoxins: Comparison Between Gamma Radiations and Accelerated Electrons", 6 pages.

Gyorgy Csako, Chao-Ming Tsai, H. Donald Hochstein, Ronald J. Elin, The Concentration , Physical State, and Purity of Bacterial Endotox Affect its Detoxification by Ionizing Radiation, 1986, 9 pages.

S. Guyomard, V. Goury, J. Laizier, J.C. Darbord, "Defining of the pyrogenic assurance level (PAL) of irradiated medical devices", Jun. 1987, 2 pages.

Davydova, Yernak, Gorback, Krassikova, Soloveva, Interaction of bacterial endotoxins with chitosan. Effect of endotoxin structure, chitosan molecular mass, and ionic strength of the solution on the formation of the complex, Sep. 2000, 1 page.

Naberezhnykh, Gorbach, Likhatskaya, Davidova, Soloveva, Interaction of chitosans and their N-acylated derivatives with lipopolysaccharide of gram-negative bacteria, Apr. 2008, 1 page.

Messerer, Halfmann, Czichy, Schulze, Awakowicz, Plasma Sterilistion and Surface Modification of Thermolabile Materials, 10 pages.

Shintani, Shimizu, Imanishhi, Sekiya, Tamazawa, Taniguchi, Kido, Inactivation of Microorganisms and Endotoxins by Low Temperature Nitrogen Gas Plasma Exposure, Mar. 2007, 13 pages.

Mosian, Barbeau, Moreau, Pelletier, Tabrizian, Yahia, Low-temperature sterilization using gas plasmas: a review of the experiments and an analysis of the inactivation mechanisms, Jul. 1000, 21 pages.

Cooper, Douglas W, "Reducing Pyrogens in Cleanroom Wiping Materials," Pharmaceutical Engineering, Jul./Aug. 1996 vol. 16, No. 4.

Office Action issued on Dec. 2, 2013 for Chinese Patent Application No. 201080061895.X.

CHITOSAN-BASED HEMOSTATIC TEXTILE

CROSS-REFERENCE TO RELATED APPLICATIONS

This application is a continuation of U.S. patent application Ser. No. 12/954,572, filed Nov. 24, 2010, which is based on and claims priority to U.S. Provisional Application Nos. 61/264,570, filed Nov. 25, 2009, and 61/350224, filed Jun. 1, 2010. The entirety of each of these priority applications is hereby incorporated by reference.

BACKGROUND

1. Field of the Invention

This invention relates to hemostatic textiles made from chitosan fibers, and more particularly to chitosan fiber-based hemostats having reduced pyrogenicity.

2. Description of the Related Art

Surgical procedures and traumatic injuries are often characterized by massive blood loss. Conventional approaches such as manual pressure, cauterization, or sutures may be time consuming and are not always effective in controlling bleeding.

Over the years, a number of topical hemostatic agents have been developed to control bleeding during surgical procedures and to control bleeding resulting from traumatic injury. Some agents such as collagen-based powders, sponges, or cloths are of a particulate nature. Particulate hemostatic agents provide a lattice for natural thrombus formation, but are unable to enhance this process in coagulopathic patients. Microfibrillar collagen, a particulate hemostatic agent, comes in powder form and stimulates the patient's intrinsic hemostatic cascade. However, this product has been reported to embolize and induce a localized inflammatory response if used during cardiopulmonary bypass. Further, particulates such as powders and even gels are difficult to control, and are easily carried away from an active bleeding site.

Pharmacologically-active agents such as thrombin can be used in combination with a particulate carrier, for example, as in a gelfoam sponge or powder soaked in thrombin. Thrombin has been used to control bleeding on diffusely bleeding surfaces, but the lack of a framework onto which the clot can adhere has limited its use. The autologous and allogenic fibrin glues can cause clot formation, but do not adhere well to wet tissue and have little impact on actively bleeding wounds.

Chitosan, the N-deacetylated derivation of chitin, has demonstrated hemostatic effectiveness as well as biocompatibility, biodegradability, and anti-bacterial activity. Chitosan has been shown to secure mucoadhesion and hemostasis despite defibrination and anticoagulation. FDA approved topical chitosan hemostats include Celox™ (a granular powder) and HemCon (a lyophilized chitosan film). Also FDA approved, for external use, is a microfibrillar high molecular weight chitosan in the form of sponge, puff or non-woven fabric.

Although chitosan has been shown to be an effective hemostat, the traditional, inexpensive methods for manufacturing commodity-grade chitosan yields a product that is laden with pyrogens, particularly endotoxins, which limit its applicability in the biological and medical arenas, as minute amounts of endotoxins may induce septic responses when contacted with mammalian tissue.

SUMMARY

Accordingly, there is a need in the art for a chitosan-based hemostatic material having reduced levels of pyrogens and/or in which the endotoxins have been removed and/or inactivated sufficiently to avoid inducing septic responses when contacted with mammalian tissue.

There is also a need in the art for such a reduced-endotoxin chitosan-based hemostat that can be made in an inexpensive manner.

Further, there is a need in the art for a process of removing and/or deactivating endotoxins in high molecular weight fibrous chitosan without substantially reducing the molecular weight of the chitosan.

In accordance with one embodiment, a method of making a hemostatic textile material is provided. The method includes processing crab shells to obtain a high molecular weight chitosan having a molecular weight in a range about 600-800 kDa and a degree of deacetylation of about 75-88%, processing the high molecular weight chitosan into a textile comprising a network of chitosan fibers, and irradiating the high molecular weight chitosan textile under nitrogen using γ-irradiation.

Another embodiment additionally comprises treating the chitosan textile under a nitrogen plasma. One such embodiment additionally comprises soaking the chitosan fibers in an alcohol prior to treating with γ-irradiation or plasma.

A further embodiment additionally comprises packaging the fibrous high molecular weight chitosan textile in a nitrogen field and sealing the package so that the chitosan textile is sealed within a nitrogen environment prior to γ-irradiation, and wherein the chitosan textile remains sealed within the package during irradiation. One such embodiment additionally comprises treating the chitosan textile under a nitrogen plasma, and the chitosan textile remains sealed within the package during nitrogen plasma treatment. Another embodiment comprises packaging the chitosan textile in a dry condition.

In one embodiment, the packaging comprises metalized packaging. Another embodiment additionally comprises forming the hemostatic chitosan textile into a woven or non-woven fabric prior to packaging the chitosan. Yet another embodiment additionally comprises treating the chitosan fibers with an acetic acid solution. In one such embodiment, the acetic acid is a glacial acetic acid so as to form an ammonium salt of chitosan.

In accordance with another embodiment, the present invention provides a method of making a textile hemostatic material. The method comprises providing a high molecular weight chitosan having a molecular weight of about 600-800 kDa and a degree of deacetylation chosen to facilitate formation of dry fibers, processing the high molecular weight chitosan into a fibrous textile, and treating the high molecular weight chitosan textile under a nitrogen plasma.

In another embodiment, the step of sterilizing the fibrous chitosan under nitrogen is configured to increase the concentration of amino groups on the chitosan fibers.

Yet another embodiment comprises treating the chitosan textile in a nitrogen plasma at ambient temperature.

In further embodiments, the chitosan has a degree of deacetylation of about 75-88%, or within a range of about 80-85%, or about 85%.

In accordance with yet another embodiment, the present invention provides a method of making a hemostatic material, comprising providing a chitosan, presenting the chitosan in a dry form, and bathing the chitosan in a field of ionized nitrogen.

In one such embodiment, providing a chitosan comprises processing crab shells.

In another embodiment, providing a chitosan comprises providing a high molecular weight chitosan formed into a fibrous form.

In a further embodiment, providing a chitosan comprises providing a fibrous high molecular weight chitosan formed into a puff or fleece.

In accordance with still another embodiment, the present invention provides a method of making a hemostatic material, comprising providing a fibrous chitosan in a dry form, placing the chitosan in a nitrogen field, and applying a treatment to the chitosan so as to ionize nitrogen in and around the chitosan.

DETAILED DESCRIPTION OF PREFERRED EMBODIMENTS

Chitosan is obtained from chitin, a widely available biopolymer obtained principally from shrimp and crab shell waste. Chitosan is the main derivative of chitin, and is the collective term applied to deacetylated chitins in various stages of deacetylation and depolymerization. The chemical structure of chitin and chitosan is similar to that of cellulose. The difference is that instead of the hydroxyl group as is bonded at C-2 in each D-glucose unit of cellulose, there is an acetylated amino group (—NHCOCH$_3$) at C-2 in each D-glucose unit in chitin and an amino group at C-2 in each D-glucose unit of chitosan.

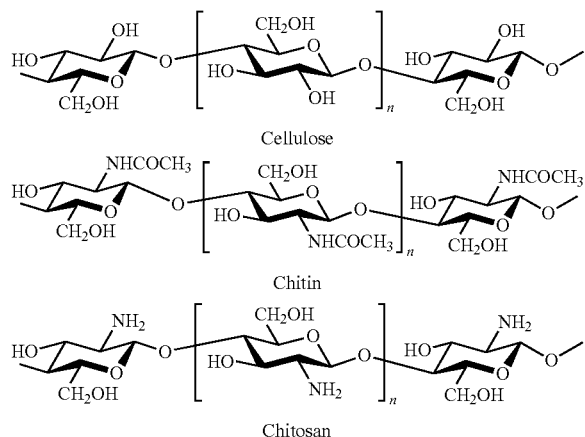

Cellulose

Chitin

Chitosan

Chitin and chitosan are both nontoxic, but chitosan is used more widely in medical and pharmaceutical applications than chitin because of its good solubility in acid solution. Chitosan has good biocompatibility and is biodegradable by chitosanase, papain, cellulase, and acid protease. Chitosan exhibits anti-inflammatory and analgesic effects, and promotes hemostasis and wound healing. Chitosan has also been shown to be an effective hemostatic agent. Chitosan hemostasis is believed to be mediated by positively charged amine groups binding to negatively charged red cell and platelet surfaces forming a mucoadhesive coagulum without activation of classical coagulation pathways.

In a preferred embodiment, a hemostatic device made from microfibrillar high molecular weight chitosan can be constructed in the form of sponge, puff or non-woven fabric. The microfibrillar high molecular weight chitosan is discussed in Applicants' copending application Ser. No. 10/868,201, filed Jun. 14, 2004, and directed to "DEPLOYABLE MULTIFUNCTIONAL HEMOSTATIC AGENT" and copending application Ser. No. 11/061,243, filed Feb. 18, 2005, and directed to a "HEMOSTATIC AGENT FOR TOPICAL AND INTERNAL USE". The entirety of both of these copending applications, and particularly the disclosure directed to making and using chitosan-based hemostatic devices, is hereby incorporated by reference.

As discussed above, chitosan is formed from chitin, which is present in crustacean shells as a composite with proteins and calcium salts. Chitin is produced by removing calcium carbonate and protein from these shells, and chitosan is produced by deacetylation of chitin in a strong alkali solution.

Figure 1:
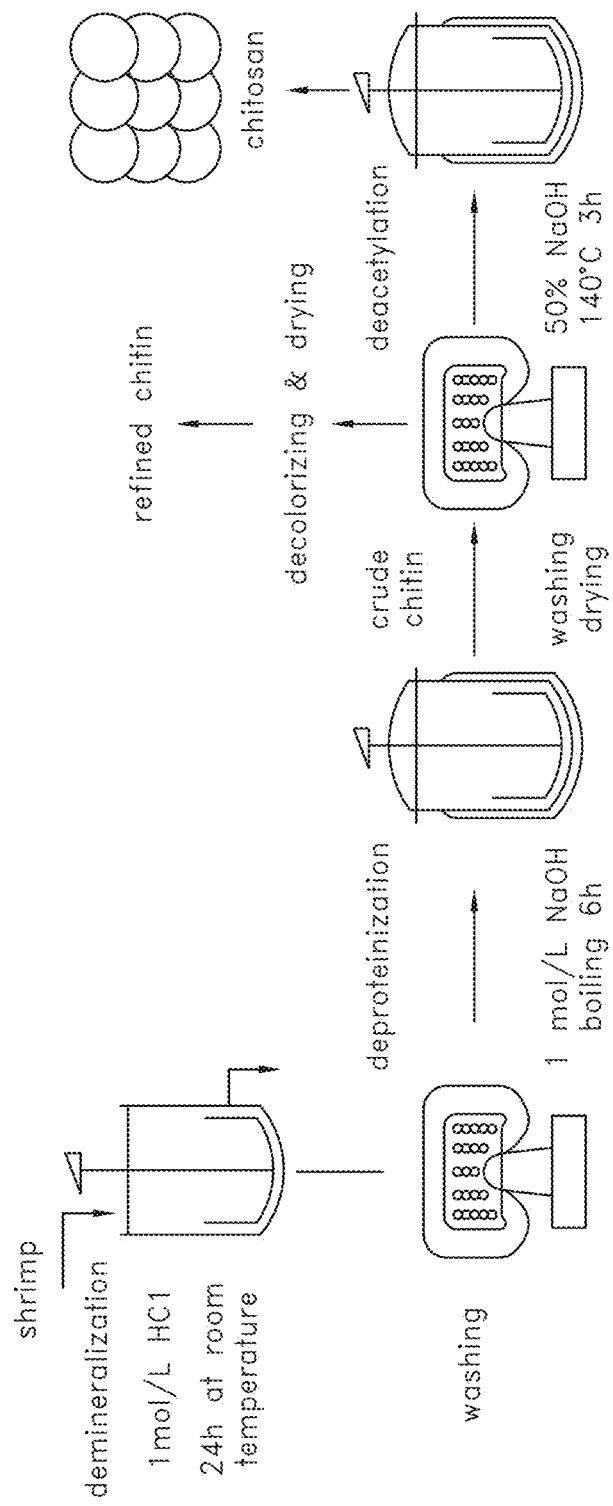
FIG. 1 schematically depicts a process for obtaining chitosan from crustacean shell waste in accordance with one embodiment.

One method for obtaining chitosan from crab, shrimp or other crustacean shells is schematically depicted in FIG. 1 and described as follows. Calcium carbonate is removed by immersing the shell in dilute hydrochloric acid at room temperature for 24 hours (demineralization). Proteins are then extracted from the decalcified shells by boiling them with dilute aqueous sodium hydroxide for six hours (deproteinization). The demineralization and deproteinization steps are preferably repeated at least two times to remove substantially all of the inorganic materials and proteins from the crustacean shells. The crude chitin thus obtained is washed then dried. The chitin is heated at 140° C. in a strong alkali solution (50 wt. %) for 3 hours. Highly deacetylated chitosan exhibiting no significant degradation of molecular chain is then obtained by intermittently washing the intermediate product in water two or more times during the alkali treatment.

Chitosan fibers can be prepared by a wet spinning method, although any suitable method could be used. In one embodiment, chitosan is first dissolved in a suitable solvent to yield a primary spinning solution. Preferred solvents include acidic solutions, for example, solutions containing trichloroacetic acetic acid, acetic acid, lactic acid, and the like, however any suitable solvent can be employed. The primary spinning solution is filtered and deaerated, after which it is sprayed under pressure into a solidifying bath through the pores of a spinning jet. Solid chitosan fibers are recovered from the solidified bath. The fibers can be subjected to further processing steps, including but not limited to drawing, washing, drying, post treatment, functionalization, and the like.

Figure 2:
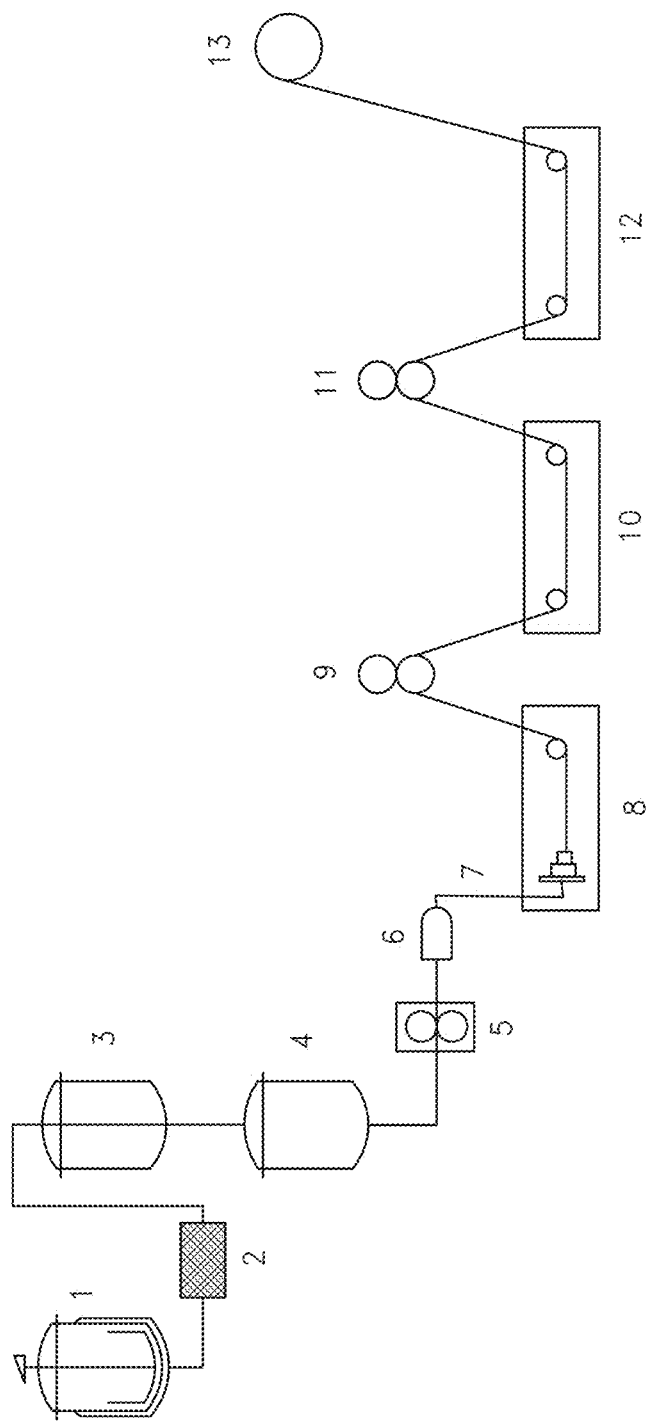
FIG. 2 schematically depicts an embodiment of an apparatus for preparing chitosan fibers.

FIG. 2 illustrates an apparatus for preparing chitosan fibers in accordance with one embodiment. The illustrated apparatus includes a dissolving kettle 1, a filter 2, a middle tank 3, a storage tank 4, a dosage pump 5, a filter 6, a spinning jet 7, a solidifying bath 8, a pickup roll 9, a draw bath 10, a draw roll 11, a washing bath 12, and a coiling roll 13.

In one embodiment, the primary chitosan spinning solution is prepared by dissolving 3 parts chitosan powder in a mixed solvent at 5° C. containing 50 parts trichloroacetic acid (TDA) to 50 parts methylene dichloride. The resulting primary spinning solution is filtered and then deaerated under vacuum. A first solidifying bath comprising acetone at 14° C. is employed. The aperture of the spinning jet is 0.08 mm, the hole count is forty-eight, and the spinning velocity is 10 m/min. The spinning solution is maintained at 20° C. by heating with recycled hot water. The chitosan fibers from the acetone bath are recovered and conveyed via a conveyor belt to a second solidifying bath comprising methanol at 15° C. The fibers are maintained in the second solidifying bath for ten minutes. The fibers are recovered and then coiled at a velocity of 9 m/min. The coiled fibers are neutralized in a 0.3 g/l KOH solution for one hour, and are then washed with deionized water. The resulting chitosan fiber is then dried, after which it is ready for fabrication into the hemostatic materials of preferred embodiments.

In one preferred embodiment, glacial, or anhydrous, acetic acid is employed as an agent to adhere the chitosan fibers to each other in embodiments where chitosan fibers, either alone or with an added medicament, therapeutic agent or other agent, are used in forming a hemostatic agent. In addition to providing good adherence between the chitosan fibers, fibers treated with glacial acetic acid also exhibit exceptional ability to adhere to wounds, including arterial or femoral wounds.

Depending upon the application, the concentration of acetic acid in solution can be adjusted to provide the desired degree of adhesion. For example, it can be desirable to employ a reduced concentration of acetic acid if the chitosan fibers are to be employed in treating a seeping wound or other wound where strong adhesion is not desired, or in applications where the hemostatic agent is to be removed from the wound. In such embodiments, an acetic concentration of from about 1 vol. % or less to about 20 vol. % is generally employed, and more preferably a concentration of from about 2, 3, 4, 5, 6, 7, 8, 9, or 10 vol. % to about 11, 12, 13, 14, 15, 16, 17, 18, or 19 vol. % is employed. Where strong adhesion between fibers, or strong adhesion to the wound is desired, a concentration greater than or equal to about 20 vol. % is preferred, more a preferably from about 50, 55, 60, 65, or 70 vol. % to about 75, 80, 85, 90, 95, or 100 vol. %, and most preferably from about 95, 96, 97, 98, or 99 vol. % to about 100 vol. %.

Figure 3:
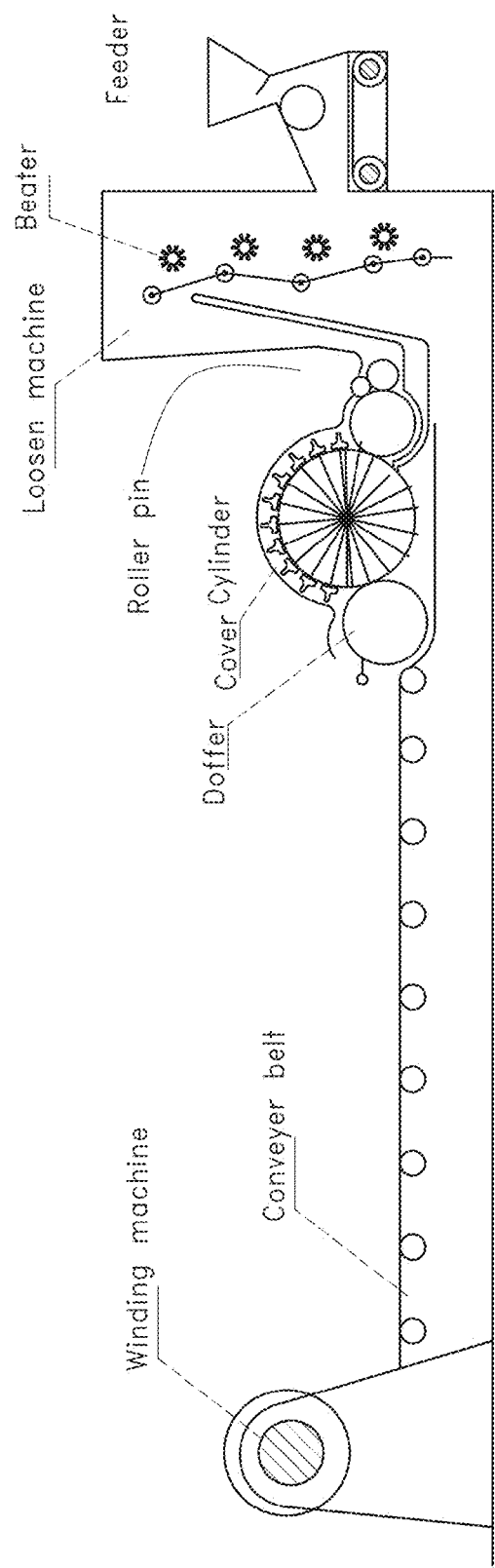
FIG. 3 provides a schematic of an assembly line for production of chitosan fleece in accordance with one embodiment.

Chitosan textile can be prepared from chitosan fibers using equipment commonly employed in the textile industry for fiber production. With reference next to FIG. 3, an assembly line for production of chitosan fleece can employ a feeder, a loosen machine, a carding machine, a conveyor belt, and lastly a winding machine, as depicted below. In the feeder, chitosan short fiber is fed through a feeder and into a loosen machine, wherein chitosan short fiber is loosened by several beaters. In the carding machine, chitosan fibers are ripped and turned into chitosan fleece by high speed spinning of a cylinder and roller pin, then the fleece is peeled off as a separated thin layer of net by a duffer.

The production of fibers and associated processing discussed above is most effective when using chitosan of relatively high molecular weight. Such high molecular weight chitosan is particularly amenable to formation into fibrous forms such as fleece that can be formed into a strong and durable textile that is flexible and malleable but retains continuity so that it can be moved as a unit and doesn't break apart when manipulated during use. In some embodiments, chitosan fibers can be formed into a yarn, which in turn can be woven. In other embodiments, successive layers of chitosan fiber pieces can be flattened and sprayed with an acidic solution (preferably a solution with a pH of about 3.0-4.5) such as the glacial acetic acid discussed above so as to form a nonwoven textile.

In accordance with preferred embodiments, a fibrous hemostatic device is constructed of high molecular weight chitosan (<600 kDA). The high molecular weight chitosan lends itself to construction of a dry, fibrous hemostatic material that can be constructed as a textile in a puff, fleece, fabric or sheet form. Embodiments of a chitosan-based hemostatic textile can be provided in many forms depending upon the nature of the wound and the treatment method employed. For example, a puff, fleece, or sponge form can be preferable for controlling active bleeding from an artery or vein, or for internal bleeding during laparoscopic procedures. In neurosurgery, where oozing brain wounds are commonly encountered, a flexible sheet form of the hemostatic material can be preferred. Likewise, in oncological surgery, especially of the liver, it can be preferred to employ a sheet form or sponge form of the hemostatic material, which is placed in or on the tumor bed to control oozing. In dermatological applications, a sheet form can be preferred. In closing punctures in a blood vessel, a puff form is generally preferred. A suture form, such as a microsuture or a macrosuture, can be preferred in certain applications.

Preferably, embodiments of microfibrillar high molecular weight chitosan are amenable to all of these applications and configurations, and embodiments are envisioned in which devices made from such chitosan are formed and shaped accordingly. Normally, however, chitosan is laden with pyrogens, particularly endotoxins, which can limit its applicability in the biological and medical arenas, as minute amounts of endotoxins may induce septic responses when contacted with mammalian tissue. As such, in accordance with some embodiments, a microfibrillar high molecular weight chitosan hemostat is used externally so as to minimize the likelihood of a septic response. In other embodiments, such chitosan hemostats can be used during surgeries, but only for temporary purposes, and are not implanted or left within a patient.

Endotoxins are essentially the skeletal or cellular remains and by-product secretions of dead bacteria, which are ubiquitous and found in the air, on surfaces and in food and water. More precisely, endotoxins are complex amphiphilic lipopolysaccharides (LPS) having both polysaccharide and lipophilic components. They are composed of pieces of the lipopolysaccharide wall component of Gram-negative bacteria. An example of LPS is shown below.

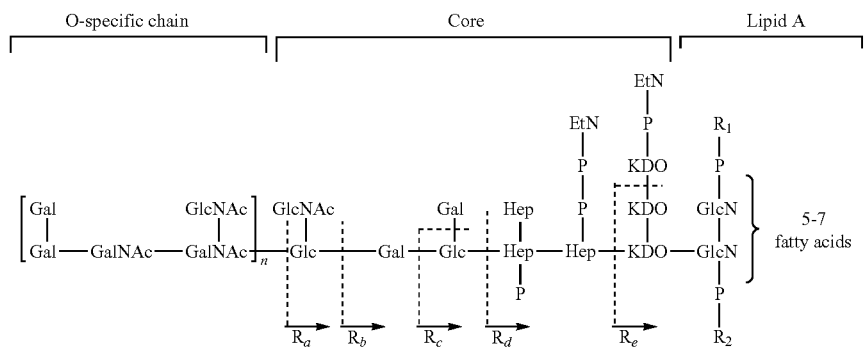

The terms endotoxin and pyrogen are often used interchangeably. Endotoxins are one of many pyrogens, which are substances that elicit a fever response in the bloodstream of a mammalian body. Vascular or lymphatic exposure to endotoxins can lead to severe sepsis, septic shock, and potential death. Thus, endotoxins are of particular concern to those manufacturing medical devices as they are one of the most potent pyrogens that can contaminate a product.

As such, pharmaceuticals, medical devices and products that contact human tissue, blood, bone or that can be absorbed by the body or implanted within the body must meet stringent levels of endotoxin control. The US Pharmacopeia have set down specifications for endotoxin units (EU) for medical devices. The current standard (USP27) specifies <20 EU per device (e.g. <0.5 EU/mL in water). Preferred embodiments of chitosan-based hemostats anticipated for internal use have sufficiently reduced levels of endotoxins to comply with such standards.

Endotoxins are notoriously difficult to remove from materials. They are extremely resilient; they are strong, tough and elastic, remain viable after steam sterilization and normal desiccation, and can pass through filters. Research shows that temperatures in excess of 200° C. for up to an hour can be required to remove endotoxin contamination.

As endotoxins are ubiquitous in biological materials, much effort and research has been dedicated to removal and/or inactivation of endotoxins in order to make biological materials useful for medical purposes. Some of the treatment methods that have been researched and employed include heat, acid base hydrolysis, oxidation, ionizing radiation such as gamma-irradiation, and ultra filtration. These methods have varying ranges of effectiveness, expense, and suitability for particular products.

It has proven difficult, however, to develop an endotoxin removal or inactivation process (depyrogenation) that is suitable for chitosan, particularly high molecular weight chitosan, as known processes such as contacting the chitosan with a strong base or γ-irradiating aqueous chitosan solutions tends to depolymerize the chitosan, resultingly decreasing the average molecular weight.

As discussed above, preferred embodiments of a chitosan-based hemostatic textile employ chitosan having very high molecular weight. Obtaining such chitosan involves important choices and procedures. A particularly preferred source of chitin for use in preparing embodiments of chitosan textiles is crab shell. Chitin prepared from crab shell, particularly arctic crab shell, generally exhibits a molecular weight that is much higher than the molecular weight of chitin made from shrimp shell. Crab shell chitin also generally exhibits a higher degree of deacetylation than shrimp shell chitin. Crab shell chitin typically exhibits an average molecular weight of from about 600-1,300 kDa. Such high molecular weight chitosan can more readily be processed to form sturdy fibers.

Preferred chitin material for use in preparing chitosan fiber in accordance with some embodiments has a molecular weight of greater than about 600, 650, 700, 750, 800, 850, 900, 950, 1000, 1100, 1200, 1300, 1400, or 1500 kDa or more; more preferably a molecular weight in a range from about 600-800 kDa; and most preferably about 700 kDA. Preferably, resulting chitosan fibers have similar molecular weights. Preferably, the chitosan preferably has a degree of deacetylation in a range between about 75-90%, more preferably in a range between about 80-88%, and most preferably in a range between about 80-85%.

In accordance with an embodiment, arctic crab shells such as Alaska snow crab shells are used as the raw material for microfibrillar chitosan. These shells preferably are washed, crushed, dried, then soaked for 12 hours in 3-5% HCl for 1-2 hours to demineralize and deproteinize the material. The slurry is transferred into a 5% NaOH reactor at 90° C. for another protein removal. Deproteinized crushed shells are washed twice with water until neutral, dried and decolorized again by exposure to ultraviolet light. Another decalcification and deproteinization follows for 12 hours in 3% HCl, followed by 3-5% NaOH 90° C. for another 1-2 hours. The deproteinized, demineralized material is washed by water to neutrality, dried and UV decolorized. At this stage the shell material has been processed to the form of chitin, and has a residual protein level ≤0.1%, which is significantly lower than commodity grade chitosan.

To process the chitin to high molecular weight chitosan in accordance with one embodiment, the material is subjected to controlled deacetylation in a 48% NaOH solution at 90° C. for 4 hours. Preferably, the degree of deacetylation (DA) is monitored by titration method to 80-88%, and more preferably about 85% as mentioned above, in order to produce high molecular weight (M.W.) chitosan (M.W. >600 kDa). Also, as noted above, crab shell chitin is unique in providing high molecular weight chitosan. Applicants have determined that high molecular weight chitosan provides a significant advantage for both endotoxin/pyrogen reduction and microfiber production in order to facilitate construction of a chitosan-based hemostatic textile.

To process high molecular weight chitosan (in preferred embodiments a high molecular weight is considered to be ≥600 kDa) in accordance with a preferred embodiment, the chitosan is dissolved in 1% trichloroacetic acid, filtered, deaerated and forced under pressure into a solidifying bath through the pores of a spinning jet (the spinneret pack). Chitosan fibers recovered from the solidified bath are washed, dried, and collected as fibers in a solidifying acetone bath (14° C.). The aperture of the spinning jet preferably is 0.8 mm (800 microns), hole count 48, and spinning velocity 10 m/min. 20° C. Chitosan fibers from the acetone bath are moved by conveyor belt to a second solidifying bath (methanol at 15° C.). Fibers are maintained in the second solidifying bath for 10 minutes, recovered, and coiled at a velocity of 9 m/min. Coiled fibers are neutralized in a 0.3 gm/L KOH solution for 1 hour before washing with deionized water, then dried, packaged and quarantined until cleared by analysis.

Chitosan processed as just discussed has been analyzed to yield the specifications as depicted in the below table, which specifications conform to the following guidelines: "ASTM F2103-01 Standard Guide for Characterization and Testing of Chitosan Salts as Starting Material Intended for Use in Biomedical and Tissue Engineered Medical Product Applications."

| Item | Specification |
|---|---|
| Bioburden, aerobic count | A total aerobic count less than 500 cfu/gram. Total aerobic, fungi, spores and obligate anaerobes under 1000 cfu/gram |
| Degree of Deacetylation | 85% |
| Average Molecular Weight | 700,000 Daltons |
| pH of $H_2O$—$C_2H_5OH$ Aq. | 5 ± 0.5 |
| Heavy Metals: Pb, Cr, Hg, Cd, As | ≤20 ppm <20 ppm total |
| Weight Loss on Drying | <15% |
| Color | White to slight yellow |
| Extractable Material | <0.1% protein |
| Solubility in Acid | <0.5% non-soluble in 1% acetic acid |

-continued

| Item | Specification |
|---|---|
| Identity | FTIR |
| Bulk Packaging for Shipping | Sealed in metalized foil bags under nitrogen |
| Residual Protein | <1% |
| Included Specifications after Microfiber, Non-woven Fabric Production | |
| Fiber Denier | Range 9.1-26.9 micron O.D. |
| In vitro adhesion | Adhesive strength (kPa ~ 70-80) |
| Chitosan structure | No change in IR spectrum after UV |

Preferably, handling and storage of the manufactured chitosan product is conducted in an endotoxin-reduced, UV irradiated environment. All bags, containers, and storage materials preferably are pyrogen free and the product is stored and transferred in a nitrogen atmosphere.

Applicants have found that high molecular weight chitosan as discussed above has less of an affinity for endotoxins than low molecular weight chitosan. Thus, although a need to inactivate endotoxins likely still exists, the high molecular weight chitosan is more amenable to successful inactivation treatment.

In one embodiment, end-product high molecular weight fibrous chitosan fleece was packaged under nitrogen. In some such embodiments, the fleece is packaged in a container made of olefin fibers such as Tyvek™. In some embodiments the packaging comprises a plastic material with or without a thin metalized layer. It is anticipated that other types of packaging may be employed. Preferably, however, the packages are sealed, keeping the fleece in an environment of nitrogen gas, and preventing entry by oxygen.

In another embodiment, packages having high molecular weight fibrous chitosan fleece prepared as discussed above and sealed in a nitrogen field such as just discussed can be irradiated with γ-irradiation ($CO^{60}$ source) at 25 kGy over 15 hours. It is anticipated and understood that other doses and intensities of γ-irradiation can be employed. However, Applicants tested chitosan fleece so prepared by implantation into rabbits to monitor the toxic response and thus evaluate the effectiveness of γ-irradiation in inactivating endotoxin contamination in high molecular weight chitosan. Applicants noted the septic response to the γ-irradiated chitosan was markedly less than that of the non-irradiated chitosan as implanted into the same rabbit. More particularly, non-irradiated chitosan exhibited substantial pus formation and localized necrosis and inflammation, while the γ-irradiated sample showed little to none of these effects.

Chitosan is graded by "purity," ranging from impure "food" or "commodity grade" to highly purified "medical grade." To qualify as "medical grade" chitosan endotoxin/pyrogen levels have to be reduced as designated by the FDA and U.S. Pharmacopeia. The endotoxin standards (USP27) for FDA approval of implantable medical devices (chitosan hemostats) are <20 EU (endotoxin units) per device or <0.5 EU/ml in water. Since endotoxin molecular weights vary (10,000 to $10^6$ Da), quantitation is measured as EU, where one EU is equivalent to 100 pg of E. coli lipopolysaccharide (LPS). These levels are typically measured by the Limulus Amoebocyte Lysate (LAL) test.

Applicants sent six samples of high molecular weight chitosan samples prepared as discussed above and γ-irradiated under nitrogen for LAL testing, along with six samples that had not been irradiated. The samples were prepared as summarized below:

| Sample Preparation: | Samples were cut and immersed: | |
|---|---|---|
| | Extraction Method: | X Immersion Fluid Pathway |
| | No. of Samples: | 6 |
| | Total Extraction Volume: | 60.0 mL |
| | Static Soak Time: | 60 minutes |
| | Extraction Temperature: | 20-25° |

The samples were then tested to detect the concentrations of EUs per device. Since certain properties of endotoxins often interfere with the results of undiluted samples, endotoxins were measured at stepped levels of dilution, with anticipated results becoming more reliable with successive dilutions. The test results follow below:

| ENDOTOXIN UNITS (EU) PER DEVICE: | Undiluted | 20.70 EU/Device |
|---|---|---|
| | 2 fold | 18.40 EU/Device |
| | 10 fold | 9.77 EU/Device |
| | 20 fold | 8.60E U/Device |

As indicated in the test results, the reliable 10 fold and 20 fold diluted test samples yield levels of EU/Device that are well within the acceptable limits for medical grade, implantable chitosan.

In contrast, the six samples that were NOT irradiated were prepared in a similar manner, yet yielded the following test results:

| ENDOTOXIN UNITS (EU) PER DEVICE: | Undiluted | >50.00 EU/Device |
|---|---|---|
| | 2 fold | 70.00 EU/Device |
| | 10 fold | 68.80 EU/Device |
| | 20 fold | 73.00 EU/Device |

The 10 fold and 20 fold diluted sample tests show levels of EU that are well beyond the acceptable levels of EU for medical grade chitosan. As the only difference in the samples was γ-irradiation in a sealed package in a nitrogen environment, Applicants have concluded that γ-irradiation of high molecular weight chitosan under these conditions effectively inactivates endotoxins. Additionally, testing of the γ-irradiated chitosan against non-irradiated chitosan for hemostatic efficacy resulted in no detectable difference.

Figure 4B:
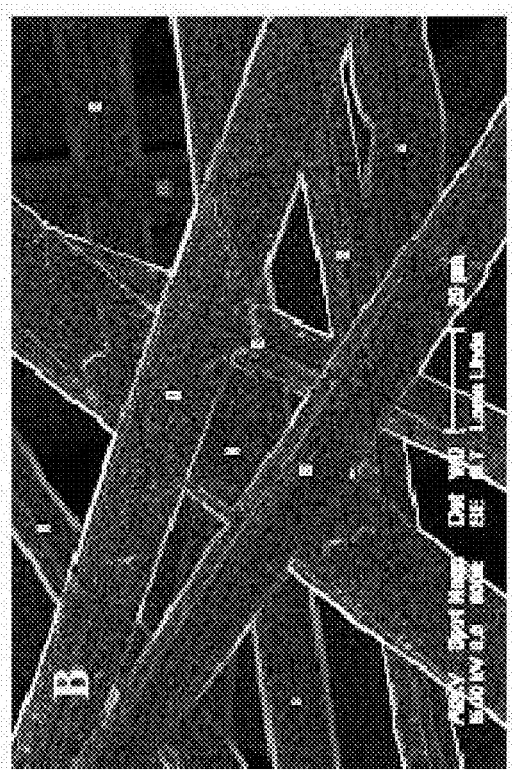
FIG. 4B is an edge enhanced image of FIG. 4A.
Figure 4A:
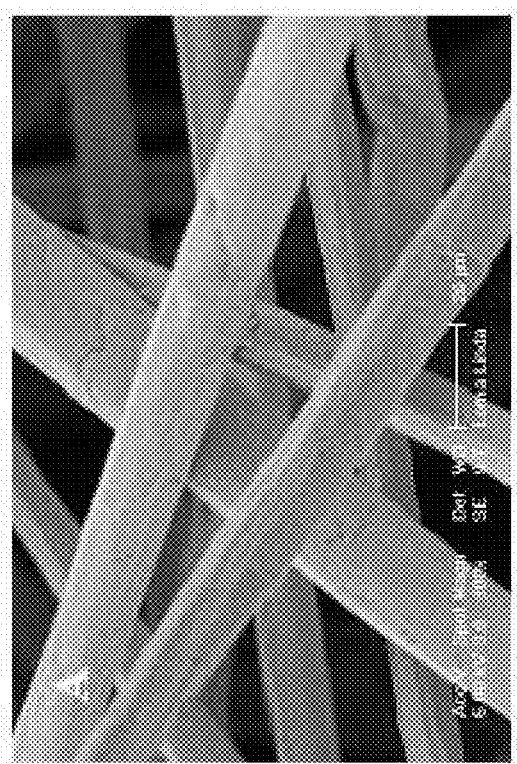
FIG. 4A is a scanning electron microscope image of a microfibrillar chitosan prepared in accordance with one embodiment.

The samples were further investigated to determine whether the γ-irradiation had caused depolymerization and/or otherwise damaged the chitosan fibers. The images in FIGS. 4A and 4B depict Scanning Electron Microscopy (SEM) surface areas of microfibrillar chitosan processed as described above and irradiated as discussed above. FIG. 4A is a SEM of microfibrillar chitosan, mean diameter of fibers 16.7±3.6 μm (range 10-26 μm). FIG. 4B is an edge enhanced image of FIG. 4A, created and analyzed using ImageJ software (ImageJ, NIH). Eleven fibers in the 150×100 μm field of view (FOV) were modeled as cylinders using fiber length and width estimates from the image. The surface area to volume ratio ($S/V_p$) of microfibrillar chitosan using the FOV dimensions and assuming a depth of six times the average fiber diameter (16.7 μm), is 4.7 $nm^{-1}$. Therefore, a dressing thickness and blood penetration depth of 5 mm, a 1×1×5 mm volume of microfibrillar chitosan presents an estimated surface area of 23.5 $μm^2$ to blood products.

In summary, the irradiated chitosan fibers were structurally intact, and maintained a high surface area that was available for interaction with blood. Applicants have concluded that the irradiation under the listed conditions caused little to no depolymerization and/or reduction in molecular weight of the chitosan fibers.

The high molecular weight chitosan fibers prepared as discussed above have a relatively high nitrogen content. Applicants have determined that treating such fibers in conditions conducive to ionization of nitrogen is especially beneficial in inactivating endotoxin without substantially damaging the chitosan fiber structure or the efficacy of the fibers in prompting hemostasis. More particularly, in some embodiments, preferably chitosan is subjected to a treatment that increases the quantity of amino groups in and around fibrous chitosan, and even more preferably a treatment that creates nitrogen-based free radicals, so as to inactivate endotoxin and simultaneously increase one or more of wetability, hydrophilicity, and mucoadhesion.

In another embodiment, a high molecular weight chitosan is treated with an ionized nitrogen gas, more specifically a nitrogen-based plasma, preferably under ambient temperature, so as to effectively inactivate endotoxins on high molecular weight chitosan without negatively affecting the efficacy or molecular weight of the chitosan.

In one embodiment, plasma treatment can be carried out using, for example, an e⁻Rio™ atmospheric pressure plasma system APPR-300-13 available from APJeT Inc. The machine uses RF electric fields, 1300 W @ 27 MHz RF/1 mm gap, to produce a unique, non-thermal, glow-discharge plasma that operates at atmospheric pressure with a cooling requirement of 1 gpm @ 20 psi max.

Figure 5:
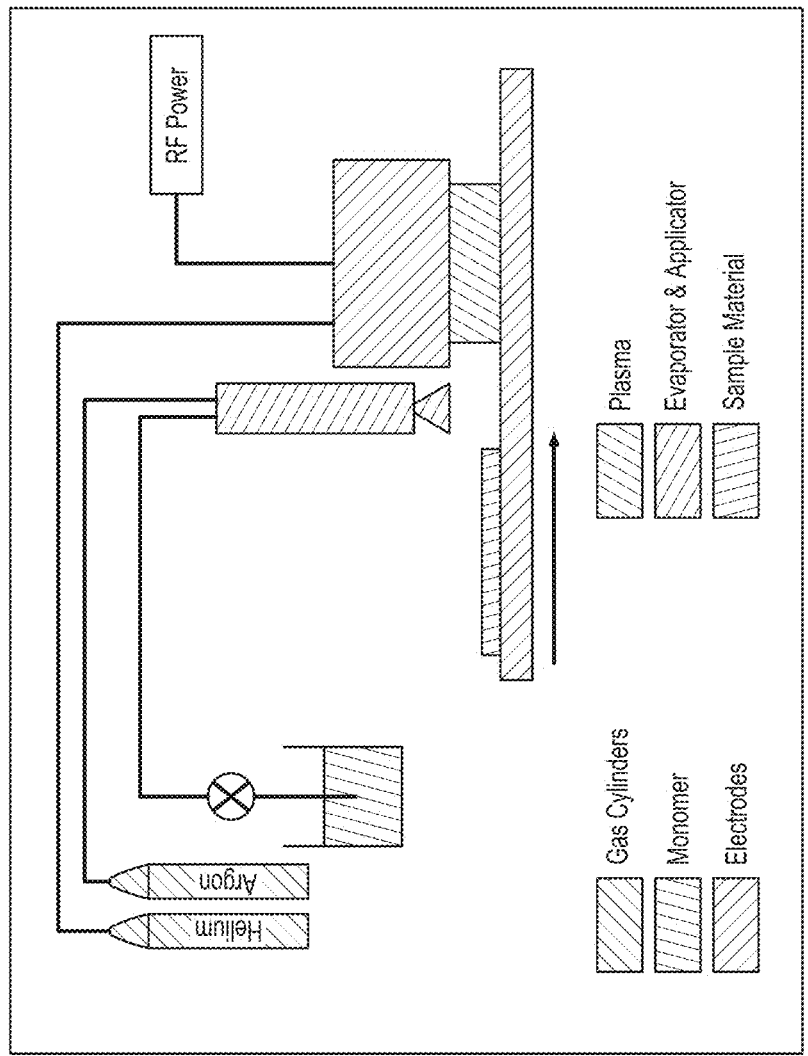
FIG. 5 is a schematic depiction of one embodiment of a plasma treatment assembly.

With reference next to the exemplary schematic in FIG. 5, in some embodiments the plasma assembly will include an evaporator and applicator. The evaporator is a heated assembly that vaporizes a monomer that is to be applied to fibrous chitosan samples. Heat is regulated by a logic controller that is connected to a thermo-coupler attached to the evaporator. The applicator acts as a heated nozzle to apply vaporized monomer to the fibrous chitosan sample. The heat maintains the vapor property of the monomer. Heat preferably is regulated by a logic controller that is connected to a thermo-coupler attached to the applicator.

It is to be understood that multiple methods and assemblies for plasma treatment of high molecular weight chitosan can be employed. For example, fibrous chitosan can be treated under a nitrogen plasma and then packaged under nitrogen gas. In some embodiments, relatively large quantities of fibrous chitosan are treated under nitrogen plasma and are then divided into individual doses and packaged separately. In still other embodiments, chitosan can be partially packaged, such as enclosed within a package having an unsealed opening, plasma-treated in the partially packaged condition, and the package may be fully sealed in the plasma treatment zone or a nearby nitrogen field.

In further preferred embodiments, high molecular weight chitosan can be packaged prior to plasma treatments. Preferably the chitosan textile is sealed in a nitrogen field, and can be prepared substantially as discussed above. In some such embodiments, the RF power activates the nitrogen within the packaging, which is believed to create nitrogen-based free radicals that contribute to deactivation of the endotoxin. Of course, it is to be understood that various types and configurations of assemblies and apparatus may be used for the plasma treatment.

Embodiments discussed above have described treating fibrous high molecular weight chitosan in a nitrogen field involving plasma, γ-irradiation, or the like. In other embodiments, other methods and apparatus that will increase the concentration of amino groups on and around the chitosan can be employed. Preferably such methods additionally provide nitrogen-based free radicals. Such methods may involve other types of irradiation, as well as variations in power, duration, and the like as compared to the examples specifically discussed herein.

In accordance with yet further embodiments, high molecular weight chitosan is treated using both plasma and a nitrogen field and γ-irradiation. In some embodiments the chitosan is first treated γ-irradiation and then treated under the plasma. In other embodiments the order is reversed.

Applicants treated samples of fibrous high molecular weight chitosan having a molecular weight about 700 kDa and a degree of acetylation of about 85%, which samples had been sealed in packages and in a nitrogen field, by first γ-irradiating the packaged samples at a level of 25 Gy, and then plasma treating the still-packaged samples. The treated samples were then subjected to LAL testing. A sample so treated under plasma for about 5 minutes was tested to have 9.6 EU/device, and 52.8 EU/gm based on a 20-fold dilution. A sample so treated under plasma for about 10 minutes was tested to have 2.3 EU/device, and 12.7 EU/gm based on a 20-fold dilution.

In some embodiments described above, fibrous chitosan is treated with an acetic acid solution so as to promote adhesion. In further embodiments, fibrous chitosan is not treated with acetic acid, and instead is subjected to γ-irradiation in a nitrogen field, nitrogen-gas based plasma treatment, and/or another treatment method that increases the concentration of amino groups on and around the chitosan so as to increase wetability, hydrophilicity and mucoadhesion without exposure to the acetic acid after being formed into a fibrous fleece.

It is to be understood that further treatments may enhance hemostatic, chitosan-based textiles. For example, in one embodiment chitosan fibers are soaked in alcohol, preferably for about an hour. In experiments, such a treatment caused the chitosan fibers to be much whiter, but with no structure change of the chitosan fiber. The total bacterial count of the chitosan fibers was also reduced. Such treated textiles can then be further treated using γ-irradiation, plasma, or both.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A method of making a hemostatic device, comprising:
   irradiating a hemostatic device comprising endotoxin-containing chitosan in a dry condition under a nitrogen plasma in a presence of γ-irradiation, whereby an amount of endotoxins present in the device is reduced to less than 20 E.U. per device, wherein after irradiating the chitosan is not substantially reduced in molecular weight.

2. The method of claim 1, wherein irradiating is conducted at ambient temperature.

3. The method of claim 1, wherein the amount of endotoxins is measured by a Limulus Amoebocyte Lysate test.

4. The method of claim 1, wherein the amount of endotoxins is measured by a Limulus Amoebocyte Lysate test at 10 fold dilution.

5. The method of claim 1, wherein the amount of endotoxins is measured by a Limulus Amoebocyte Lysate test at 20 fold dilution.

6. The method of claim 1, wherein the irradiated hemostatic device has an amount of endotoxins of less than or equal to 9.77 E.U. per device at 10 fold dilution.

7. The method of claim 1, wherein the irradiated hemostatic device has a concentration of endotoxins of no greater than 9.6 E.U. per device at 20 fold dilution.

8. The method of claim 1, wherein the irradiating is conducted under γ-irradiation at 25 kGy for 15 hours.

9. The method of claim 1, wherein the nitrogen-based plasma consists essentially of nitrogen plasma.

10. The method of claim 1, wherein the nitrogen-based plasma consists of nitrogen plasma.

11. The method of claim 1, wherein the chitosan of the hemostatic device is in fibrous form.

12. The method of claim 1, wherein the chitosan of the hemostatic device is in powder form.

13. The method of claim 1, wherein the chitosan of the hemostatic device is in film form.

14. The method of claim 1, wherein the chitosan of the hemostatic device is in sheet form.

15. The method of claim 1, wherein the chitosan of the hemostatic device is in sponge form.

16. The method of claim 1, wherein the chitosan of the hemostatic device is in a form of a woven or nonwoven textile.

17. The method of claim 1, wherein the hemostatic device comprising chitosan is a microsuture or a macrosuture.

* * * * *

UNITED STATES PATENT AND TRADEMARK OFFICE
CERTIFICATE OF CORRECTION

PATENT NO. : 8,932,521 B2  
APPLICATION NO. : 14/097151  
DATED : January 13, 2015  
INVENTOR(S) : Wolff M. Kirsch et al.

Page 1 of 1

It is certified that error appears in the above-identified patent and that said Letters Patent is hereby corrected as shown below:

On the Title Page:

In column 2 (page 2, item 56) at line 10, Under Other Publications, change "Endotox" to --Endotoxin--.

In column 2 (page 2, item 56) at lines 22-23, Under Other Publications, change "Sterilistion" to --Sterilisation--.

In the Drawings:

Sheet 1 of 5 (FIG. 1) at line 3 (approx.), Change "HC1" to --HCl--.

In the Specification:

In column 4 at line 12, After "to" insert --a--.

In column 4 at line 60 (approx.), Change "(TDA)" to --(TCA)--.

In column 10 at line 25, Change "8.60E U/Device" to --8.60 EU/Device--.

In column 11 at line 18, Change "wetability," to --wettability,--.

In column 12 at line 35 (approx.), Change "wetability," to --wettability,--.

Signed and Sealed this  
Twenty-second Day of March, 2016

Michelle K. Lee  
*Director of the United States Patent and Trademark Office*